United States Patent
Shi et al.

(10) Patent No.: US 7,534,881 B2
(45) Date of Patent: May 19, 2009

(54) METHOD FOR PREPARING PYRROLOTRIAZINE COMPOUNDS

(75) Inventors: Zhongping Shi, West Windsor, NJ (US); John Hynes, Washington Crossing, PA (US); Luca Parlanti, Princeton, NJ (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 380 days.

(21) Appl. No.: 11/168,682

(22) Filed: Jun. 28, 2005

(65) Prior Publication Data

US 2006/0003967 A1    Jan. 5, 2006

Related U.S. Application Data

(60) Provisional application No. 60/584,382, filed on Jun. 30, 2004.

(51) Int. Cl.
  *C07D 487/04*  (2006.01)
  *C07D 207/30*  (2006.01)
  *C07D 207/50*  (2006.01)

(52) U.S. Cl. .................. 544/183; 548/530; 548/557

(58) Field of Classification Search .................. 544/183; 548/557, 530
  See application file for complete search history.

(56) References Cited

U.S. PATENT DOCUMENTS

| | | | |
|---|---|---|---|
| 6,670,357 | B2 | 12/2003 | Leftheris et al. |
| 6,867,300 | B2 | 3/2005 | Godfrey, Jr. et al. |
| 6,869,952 | B2 | 3/2005 | Bhide et al. |
| 6,906,067 | B2 | 6/2005 | Moriarty et al. |
| 6,908,916 | B2 | 6/2005 | Mastalerz et al. |
| 6,916,815 | B2 | 7/2005 | Vite et al. |
| 6,933,386 | B2 | 8/2005 | Bhide et al. |
| 6,951,859 | B2 | 10/2005 | Bhide et al. |
| 6,962,915 | B2 | 11/2005 | Das et al. |
| 6,969,717 | B2 | 11/2005 | Bhide et al. |
| 6,982,265 | B1 | 1/2006 | Hunt et al. |
| 2002/0065270 | A1 | 5/2002 | Moriarty et al. |
| 2003/0139435 | A1 | 7/2003 | Ahmed et al. |
| 2003/0232831 | A1 | 12/2003 | Dyckman et al. |
| 2004/0082582 | A1 | 4/2004 | Dyckman et al. |
| 2004/0157846 | A1 | 8/2004 | Chen et al. |
| 2004/0229877 | A1 | 11/2004 | Leftheris et al. |
| 2005/0043306 | A1 | 2/2005 | Leftheris et al. |
| 2005/0143398 | A1 | 6/2005 | Das et al. |
| 2005/0182058 | A1 | 8/2005 | Fink et al. |
| 2005/0197339 | A1 | 9/2005 | Gavai et al. |
| 2005/0209454 | A1 | 9/2005 | Swaminathan et al. |
| 2005/0245530 | A1 | 11/2005 | Borzilleri et al. |
| 2006/0004067 | A1 | 1/2006 | Chen et al. |
| 2006/0009454 | A1 | 1/2006 | Gai et al. |
| 2006/0014745 | A1 | 1/2006 | Gavai et al. |
| 2006/0019928 | A1 | 1/2006 | Lin et al. |
| 2006/0030708 | A1 | 2/2006 | Lobben |

FOREIGN PATENT DOCUMENTS

| | | |
|---|---|---|
| WO | WO-96/39389 A1 * | 12/1996 |
| WO | WO 00/71129 | 11/2000 |
| WO | WO 03/042172 | 5/2003 |
| WO | WO 03/090912 | 11/2003 |
| WO | WO 03/091229 | 11/2003 |
| WO | WO 2004/009601 | 1/2004 |
| WO | WO 2004/009784 | 1/2004 |
| WO | WO 2004/013145 | 2/2004 |
| WO | WO 2005/077945 | 8/2005 |

OTHER PUBLICATIONS

Carpino et al., J. Org. Chem., 30, 736-739, 1965.*
Carpino, et al., J. Am. Chem. Soc. 1959, 81, 955-957, 1959.*
Marmer, et al., J. Org. Chem., 37, 3520-3523.*
Parlanti et al., Organic Letters, 9(19), 3821-3824, 2007.*
Shen et al., J. Org. Chem. 2002, 67, 6236-6239.*
Carpino et al., J. Org. Chem. 1965, 30, 321-323.*
PubChem: Compound List, 1-49, 2008. Search Date Aug. 16, 2008.*
Greene, T. W. et al., "Protective Groups in Organic Synthesis", Table of Contents, Wiley, NY (1999)

* cited by examiner

*Primary Examiner*—Venkataraman Balasubramanian
(74) *Attorney, Agent, or Firm*—Laurelee A. Duncan

(57) ABSTRACT

A method for aminating pyrrole derivatives and for preparing pyrrolotriazine compounds having the formula V,

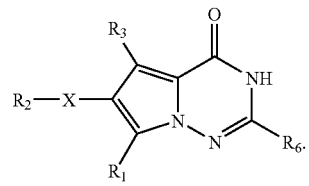

9 Claims, No Drawings

METHOD FOR PREPARING PYRROLOTRIAZINE COMPOUNDS

RELATED APPLICATIONS

This application claims priority benefit under Title 35 § 119(e) of U.S. provisional Application No. 60/584,382, filed Jun. 30, 2004, the contents of which are herein incorporated by reference.

FIELD OF THE INVENTION

The invention relates to methods for preparing pyrrolotriazine compounds useful as components or precursors in the synthesis of pharmaceutical compounds having utility as anti-cancer agents and kinase inhibitors. The invention also includes an efficient method of aminating pyrrole compounds useful in the synthesis of pyrrolotriazines and other N-aminated heterocyclic compounds.

BACKGROUND OF THE INVENTION

Pyrrolotriazine-containing compounds have been found to be useful as anti-cancer agents as well as kinase inhibitors. See, e.g., WO 00/71129, WO 03/042172, WO 04/013145, WO 04/009784, WO 04/009601, WO 03/090912, WO 03/091229, and U.S. Pat. No. 6,670,357, which are commonly assigned to Bristol-Myers Squibb Co. The entire disclosure of each of the foregoing patent applications, patents, and publications is incorporated herein by reference.

SUMMARY OF THE INVENTION

This invention is directed to various methods for preparing pyrrolotriazine compounds as recited in the claims appended hereto. A pyrrolotriazine compound has the following formula V,

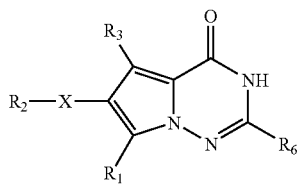

V wherein:

$R_1$ and $R_3$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2 OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2 NR_bR_c$, $NR_dP(=O)_2NR_bR_c$, $NR_bC(=O)R_a$, or $NR_bP(=O)_2R_e$;

X is —O—, —OC(=O)—, —S—, —S(=O)—, —S(=O)$_2$—, —C(=O)—, —C(=O)O—, —NR$_d$—, —NR$_d$C(=O)—, —C(=O)NR$_d$—, —NR$_d$C(=O) NR$_d$—, —NR$_d$C(=O)O—, —OC(=O)NR$_d$—, —NR$_d$S(=O)$_2$—, —NR$_d$S(=O)$_2$NR$_d$—, —S(=O)$_2$NR$_d$—, halogen, nitro, cyano, or a bond;

$R_2$ is selected from:
a) hydrogen, provided that $R_2$ is not hydrogen if X is —S(=O)—, —SO$_2$—, —OC(=O)—, —OC(=O) NR$_d$—, or —S(=O)$_2$NR$_d$—;
b) alkyl or substituted alkyl, alkenyl or substituted alkenyl, and alkynyl or substituted alkynyl, cycloalkyl or substituted cycloalkyl, cycloalkenyl or substituted cycloalkenyl;
c) heterocycle or substituted heterocycle, aryl or substituted aryl; and
d) $R_2$ is absent if X is halogen, nitro, or cyano;

$R_1$ and $R_2$ together may optionally form a 3-7 membered optionally substituted carbocyclic ring or 3-7 membered optionally substituted heterocyclic ring;

$R_6$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

This invention is also directed to a method of aminating pyrrole derivatives useful in the synthesis of pyrrolotriazines and other N-aminated heterocyclic compounds.

DETAILED DESCRIPTION OF THE INVENTION

Abbreviations

For ease of reference, the following abbreviations are employed herein, including the methods of preparation and Examples that follow:

AP=area percent in HPLC
t-Bu=tertiary butyl
Me=methyl
dec.=decomposed
Et=ethyl
EtOAc=ethyl acetate
OMe=methoxyl
OEt=ethoxyl
Boc=tert-butyloxycarbonyl
DCM=dichloromethane
DMF=dimethyl formamide
NMP=1-methyl-2-pyrrolidinone
DMSO=dimethyl sulfoxide
THF=tetahydrofuran
Et$_3$N=triethylamine
CSA=camphorsulfonic acid
MeSO$_3$H=methanesulfonic acid
EtSO$_3$H=ethanesulfonic acid
TsOH=p-toluenesulfonic acid
PhSO$_3$H=phenylsulfonic acid
4-NO$_2$-PhSO$_3$H=4-nitrophenylsulfonic acid KOtBu=potassium t-butoxide
min=minute(s)
L=liter
mL=milliliter
g=gram(s)
mg=milligram(s)
mol=moles
mmol=millimole(s)
RT or rt=room temperature
sat or sat'd=saturated
aq.=aqueous
HPLC=high performance liquid chromatography
MS=mass spectrometry
NMR=nuclear magnetic resonance
mp or Mp=melting point Definitions The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_e$ are independently hydrogen, alkyl, cycloalkyl, heterocycle, aryl, or said $R_b$ and $R_e$ together with the N to which they are bonded optionally form a heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro- 1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e.,=O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" or "halo" refer to chlorine (Cl), bromine (Br), fluorine (F) or iodine (I).

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

The compounds of present invention may form salts which are also within the scope of this invention. Reference to compounds of the formula I through V herein is understood to include reference to salts thereof, unless otherwise indicated. The term "salt(s)", as employed herein, denotes acidic and/or basic salts formed with inorganic and/or organic acids and bases. In addition, when a compound contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting those compounds with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield compounds of the formula I through V, or a salt and/or solvate thereof. Solvates of the compounds of formulas I through V include, for example, hydrates.

Compounds of the formulas I through V, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Methods of Preparation

The methods for preparing pyrrolotriazine compounds are illustrated in the following schemes. Solvents, temperatures, pressures, and other reaction conditions may readily be selected by one of ordinary skill in the art. Starting materials are commercially available or readily prepared by one of ordinary skill in the art.

The aminating reagent of formula III can be prepared according to Scheme 1, wherein $R_4$ is H, $C_1$-$C_4$ alkyl, nitro, cyano, halogen, OMe, or OEt, and n is 1, 2, or 3. For example, a salt form of benzoyl hydroxyl amine of formula IV can be obtained by reacting a benzoyl chloride of formula (1) with a hydroxyl amine, such as N-Boc-hydroxyamine, in the presence of a base, such as triethylamine, followed by addition of an acid H—Y, such as $MeSO_3H$, $EtSO_3H$, TsOH, CSA, 4-$NO_2$-$PhSO_3H$, $CF_3SO_3H$, HCl, $H_3PO_4$, $HNO_3$, $H_2SO_4$, $PhSO_3H$, or HBr. The free hydroxyl amine of formula III can be prepared by treating the salt of formula IV with a base, such as aq. $NaHCO_3$, in an organic solvent, such as $CH_2Cl_2$.

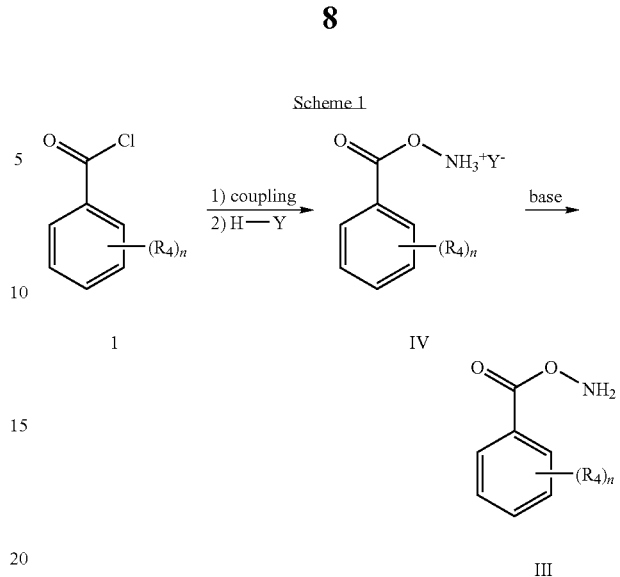

A pyrrolotriazine of formula V can be prepared according to Scheme 2, wherein X, $R_1$, $R_2$, $R_3$, $R_4$, n, and $R_6$ are as defined above, and D is —C(=O)$OR_p$ in which $R_p$ is H, $C_1$-$C_6$ alkyl, or aryl, and preferably $R_p$ is Me or Et. An aminopyrrole of formula II can be synthesized by reacting a pyrrole of formula I with the aminating reagent of formula III in the presence of a base, such as KOtBu, in an aprotic solvent, such as NMP. Cyclization of compound II with an amide of formula $R_6$C(=O)$NH_2$, preferably in the presence of an acid, forms the compound of formula V.

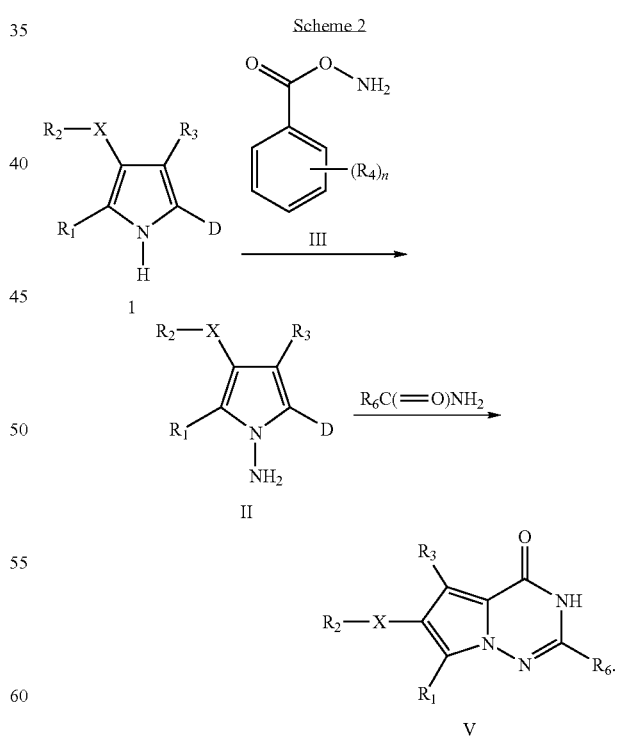

Alternatively, the compound of formula V can be prepared according to Scheme 3, wherein $R_1$, X, $R_2$, $R_3$, $R_4$, n, and $R_6$ are as defined above. The pyrrole of formula Ia is reacted with the aminating reagent of formula III in the presence of a base, such as KOtBu, in an aprotic solvent, such as NMP, followed by treatment under cooling with a base such as KOH, to form compound Ia.

Compound IIa is reacted with an aq. base such as KOH at rt to form compound IIb. Compound IIb is reacted with an acylating agent of formula $R_6(=O)—W$, wherein W is Cl or OH, such as formic acid, in an aq. solvent, to form compound IIc. Compound IIc is cyclized with a base, such as sodium methoxide, in an organic solvent, such as MeOH, with heating to form compound V.

Compounds Ia may be obtained from substituted pyrroles by formylation, e.g., by reaction with phosphorus oxychloride and DMF. A methylpyrrole may be obtained by reduction of a formylpyrrole, e.g., by reaction with lithium aluminum hydride.

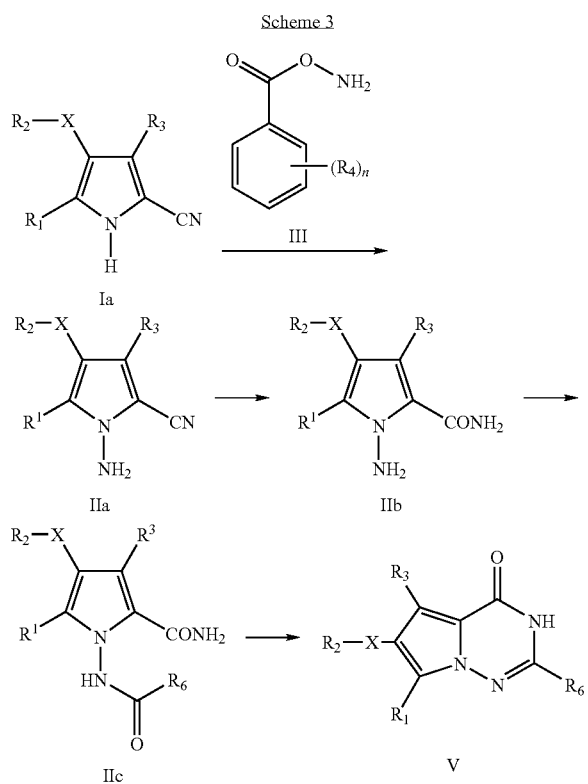

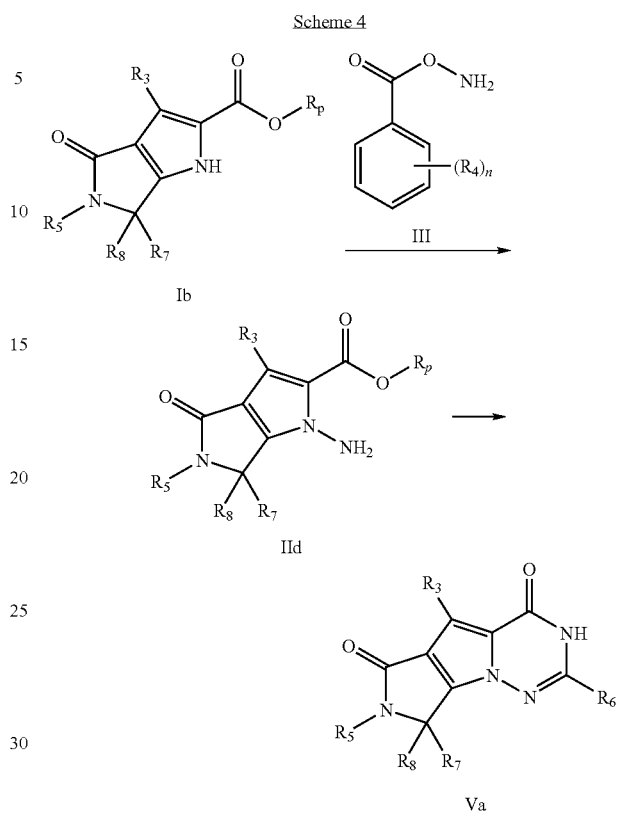

Additionally, as shown in Scheme 4, a pyrrole derivative of formula Ib can be reacted with the aminating reagent of formula III in the presence of a base, such as KOtBu, in an aprotic solvent, such as NMP, to form a compound of formula IId. Cyclization of compound IId with an amide of formula $R_6C(=O)NH_2$, preferably in the presence of an acid, forms a compound of formula Va. In Scheme 4, $R_3$ and $R_6$ are defined as above; $R_5$ is hydrogen, alkyl or substituted alkyl, alkenyl or substituted alkenyl, cycloalkyl or substituted cycloalkyl, aryl or substituted aryl, or heterocycle or substituted heterocycle; $R_7$ and $R_8$ are each independently hydrogen, alkyl or substituted alkyl, alkenyl or substituted alkenyl, cycloalkyl or substituted cycloalkyl, halogen, cyano, nitro, aryl or substituted aryl, heterocycle or substituted heterocycle, $OR_a$, $SR_a$, or $NR_bR_c$; and $R_p$ is alkyl or substituted alkyl, or aryl or substituted aryl, preferably $R_p$ is $C_1$-$C_4$ alkyl, more preferably $R_p$ is Me or Et.

The following examples are provided to describe the invention in further detail. These examples are intended to illustrate and not to limit the invention.

EXAMPLES

HPLC condition used in the following examples:
Column: Waters XTerra RP-18, 4.6×50 mm, 3.5 micron;
Mobile phase: solvent A—0.2% aqueous H3PO4; solvent B—MeCN/water (90/10);
Flow rate: 2.5 ml/min;
Linear gradient time: 8 min (Start solvent % B=1; Final solvent % B=100); and
Wave length: 256 nm.

Example 1

Preparation of Compound 2:

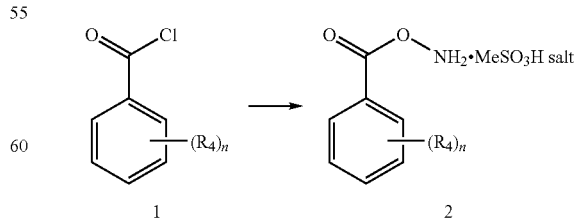

Triethylamine (5.82 g, 57 mmol) was added to a solution of N-Boc-hydroxyamine (6.80 g, 50 mmol) in 30 mL of dichloromethane at room temperature. The solution was cooled to 0° C. A solution of 3,4,5-trimethoxylbenzoyl chloride (Compound 1, wherein $(R_4)_n$ is 3,4,5-trimethoxy, 11.9 g, 52 mmol) in dichloromethane (40 mL) was slowly added to the solution at 0-5° C. over 35 minutes. The resulted mixture was stirred at 0-5° C. for 5 minutes and then warmed up to 15-20° C. for 1 h. Water (45 mL) was added to quench the reaction. After stirring for 20 minutes, the organic layer was separated, washed with aqueous $NaHCO_3$ (1%, 35 mL), and then treated with methanesulfonic acid (8.15 g, 84.9 mmol) at rt for 16 h. The mixture was treated heptane (20 mL) for 20 minutes. The white solid was collected by filtration and wash with heptane-dichloromethane (1:2, 35 mL). The wet cake was dried under vacuum at 40° C. for 16 h to give 14.4 g (87%) of product 2 (X=3,4,5-trimethoxyl) as a white solid. Mp 157-159° C. (dec.). $^1$H NMR (DMSO-D6, 400 MHz) δ 9.06 (br s, 3H), 7.25 (s, 2H), 3.86 (s, 6H), 3.78 (s, 3H), 2.45 (s, 3H). $^{13}$C NMR (DMSO-D6, 100 MHz) 163.7, 152.8 (2C), 142.6, 121.0, 106.5 (2C), 60.1, 56.0 (2C), 39.9.

Example 2

Preparation of Compound 3:

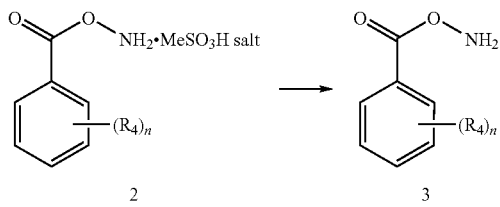

A solution of aqueous $NaHCO_3$ (6%, 20 mL) was added to a slurry of O-4-methoxyl benzoyl hydroxylamine methanesulfonate salt (Compound 2, wherein $(R_4)_n$ is 4-OMe, 4.55 g, 17.3 mmol) in dichloromethane (40 mL) at rt. After stirring for 15 minutes, the organic layer was separated and the aqueous layer was extracted with dichloromethane (20 mL). The combined organic layers were treated with heptane (30 mL) and concentrated to about 30 mL. The resulted slurry was stirred at rt for 1 h. The white solid was collected by filtration and wash with heptane (10 mL). The wet cake was dried under vacuum at rt for 20 h to give 2.6 g (89%) Compound 3 $((R_4)_n$=4-OMe) as a white solid. mp 34-35° C. $^1$H NMR (CDCl$_3$, 400 MHz) δ 7.97 (d, 2H, J=8.8 Hz), 6.93 (d, 2H, J=8.8 Hz), 6.58 (br s, 2H), 3.86 (s, 3H). $^3$C NMR (CDCl$_3$, 100 MHz) 167.4, 163.8, 131.5 (2C), 120.3, 113.9 (2C), 55.5.

Example 3

Alternative Preparation of Compound 3:

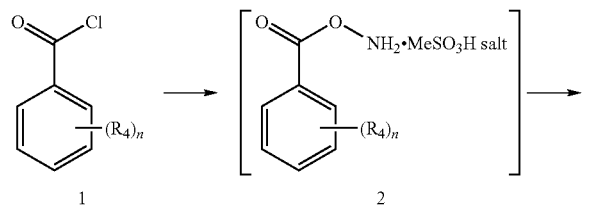

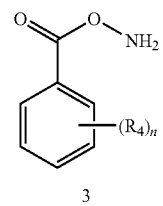

Triethylamine (40.7 g, 402 mmol) was added to a solution of N-Boc-hydroxyamine (50.0 g, 368 mmol) in 200 mL of dichloromethane at room temperature. The solution was cooled to 0° C. A solution of 4-nitrobenzoyl chloride (Compound 1, wherein $(R_4)_n$ is 4-nitro, 69.1 g, 365 mmol) in dichloromethane (320 mL) was slowly added to the solution at 0-5° C. over 65 minutes. The resulted mixture was stirred at 0-5° C. for 5 minutes and then warmed up to 15-20° C. Water (300 mL) was added to quench the reaction. After stirring for 5 minutes, the organic layer was separated, washed with aqueous $K_2HPO_4$ (4%, 200 mL), and then treated with methanesulfonic acid (52.6 g, 548 mmol) at rt for 20 h. The mixture was treated with aqueous $K_2HPO_4$ (20%, 610 g) at rt for 5-10 minutes. Tetrahydrofuran (520 mL) was added to the mixture. The organic layer was separated, washed with brine (25%, 530 g), and dried over $Na_2SO_4$ (50 g) for 30 minutes. After removal of $Na_2SO_4$ by filtration, the filtrate was concentrated under vacuum at 25-35° C. to about 355 g. Heptane (440 mL) was slowly added to the mixture for crystallization. The solid was collected by filtration, wash with THF-heptane (1:2, 90 mL), and drying under vacuum at 25-35° C. to give a slightly yellow product of Compound 3 $((R_4)_n$=4-nitro, 56.6 g, 85%, 99.2 AP). Mp. 85° C. (dec.). $^1$H NMR (CDCl$_3$, 400 MHz) δ 8.32 (d, 2H, J=8.4 Hz), 8.21(d, 2H, J=8.4 Hz), 6.76 (s, 2H). $^{13}$C NMR (CDCl$_3$, 100 MHz) 1675.5, 150.8, 133.3, 130.6 (2C), 123.7 (2C).

Example 4

Preparation of Compound 5:

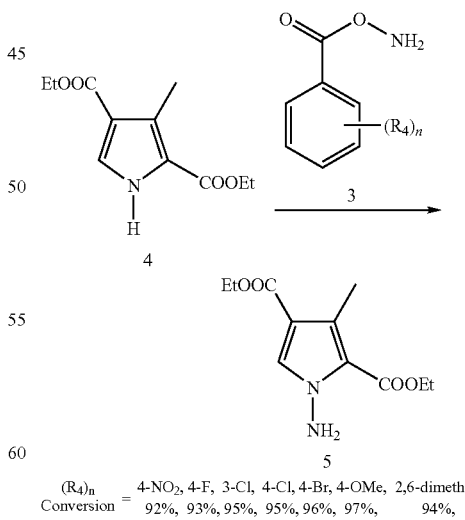

| $(R_4)_n$ Conversion | 4-NO$_2$, 92%, | 4-F, 93%, | 3-Cl, 95%, | 4-Cl, 95%, | 4-Br, 96%, | 4-OMe, 97%, | 2,6-dimethoxy, 94%, | 3,4,5-trimethoxy, 94%, | 2,4, dimethoxy. 91%. |

A solution of potassium t-butoxide in THF (1 M, 1.1 mL) was added to a solution of Compound 4 (225 mg, 1 mmol) in NMP (1-methyl 2-pyrrolidinone, 1.3 mL) at 20° C. After 15 minutes, a solution of aminating reagent 3 (1.1 mmol) in NMP (0.8 mL) was added to the solution at 20° C. while stirring. The mixture was stirred at 20° C. for 20 minutes to 6 h. The conversion of Compound 4 was determined by HPLC analysis. The reaction mixture was treated with brine (7%, 4 mL) and toluene (4 mL). The organic layer was separated and the aqueous layer was extracted with toluene (4 mL). The combined organic layers were washed with aqueous sodium bicarbonate solution (5%, 3 mL) and water (2 mL). Concentration of the solution gave a crude Compound 5 (~240 mg). $^1$H NMR (CDCl$_3$, 400 MHz) δ 7.57 (s, 1H), 4.85 (br s, 2H), 4.35 (q, 2H, J=7.1 Hz), 4.26 (q, 2H, J=7.1 Hz), 2.57 (s, 3H), 1.39 (t, 3H, J=7.1 Hz), 1.33 (t, 3H, J=7.1 Hz). $^{13}$C NMR (CDCl$_3$, 100 MHz) 164.7, 162.9, 132.4, 130.7, 120.0, 111.9, 60.8, 60.0, 14.8, 14.7, 14.4. The same transformation was achieved using the aminating reagent 3, wherein (R$_4$)$_n$ is 4-nitro, 4-F, 3-Cl, 4-Cl, 4-Br, 4-OMe, 2,6-dimethoxy, 3,4,5-trimethoxy, or 2,4-dimethoxy, and the corresponding conversions were listed above.

Example 5

Alternative Preparation of Compound 5:

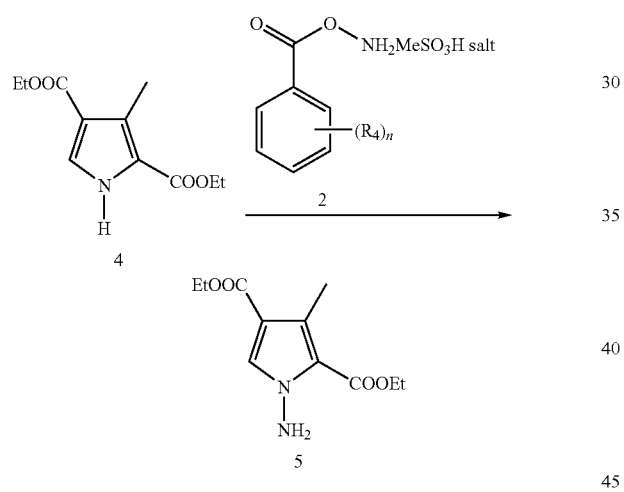

A mixture of aminating reagent salt (Compound 2, wherein (R$_4$)$_n$ is 4-methyl, 820 mg, 3.3 mmol), dichloromethane (9 mL), and aqueous NaHCO$_3$ (6%, 5 mL) was stirred at rt for 15 minutes. The organic layer was separated and dried over anhydrous sodium sulfate (2 g). After the solid sodium sulfate was removed by filtration, DMF (2.2 mL) was added to the filtrate. Concentration of the filtrate under vacuum at rt to remove dichloromethane gave a solution of aminating reagent 3 (free base as shown in Example 3, wherein (R$_4$)$_n$ is 4-methyl) in DMF. In another reaction container was added Compound 3 (225 mg, 1 mmol), N-methyl-2-pyrrolidinone (1.1 mL), and potassium t-butoxide (1 M in THF, 1.08 mL). To this mixture was added the above aminating reagent 3 in DMF (0.9 mL) at rt. After stirring at rt for 1.5 h, the reaction mixture was treated with brine (7%, 4 mL) and toluene (4 mL). The organic layer was separated and the aqueous layer was extracted with toluene (4 mL). The combined organic layers were washed with aqueous sodium bicarbonate solution (5%, 3 mL) and water (2 mL). Concentration of the solution gave a crude Compound 5 (240 mg, 94% pure by HPLC).

A similar transformation was achieved using aminating reagent 3 wherein (R$_4$)$_n$ is H, and the conversion was 91%.

Example 6

Preparation of Compound 6:

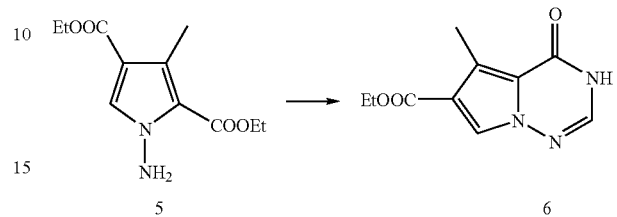

The crude Compound 5 (21 g) was treated with formamide (160 mL) and phosphoric acid (85%, 1.45 g). The mixture was heated to 120-125° C. for 18 h and then cooled to 90° C. Water (140 mL) was slowly added to the mixture over 45 minutes for crystallization. The mixture was cooled to rt for 1-4 h. The solid was collected by filtration, washed with water (2×80 mL) and toluene (120 mL), and dried under vacuum at 55° C. to give Compound 6 (13.8 g, 70%, 99.4 AP). Mp 215° C. (dec.). $^1$H NMR (DMSO-D6, 400 MHz) δ 11.65 (br s, 1H), 7.87 (s, 1H), 7.85 (s, 1H), 4.24 (q, 2H, J=7.0 Hz), 2.61 (s, 3H), 1.30 (t, 3H, J=7.0 Hz). $^{13}$C NMR (DMSO-D6, 100 MHz) δ 163.4, 155.1, 140.0, 123.2, 122.9, 117.7, 114.0, 59.6, 14.2, 11.0.

We claim:

1. A method for preparing a compound of formula II,

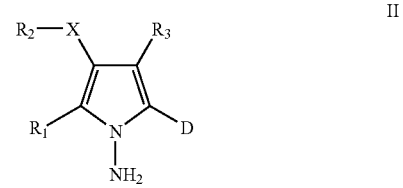

II wherein:

R$_1$ and R$_3$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

X is —O—, —OC(=O)—, —S—, —S(=O)—, —S(=O)$_2$—, —C(=O)—, —C(=O)O—, —NR$_d$—, —NR$_d$C(=O)—, —C(=O)NR$_d$—, —NR$_d$C(=O)NR$_d$—, —NR$_d$C(=O)O—, —OC(=O)NR$_d$—, —NR$_d$S(=O)$_2$—, —N$_d$S(=O)$_2$NR$_d$—, —S(=O)$_2$NR$_d$—, halogen, nitro, cyano, or a bond;

R$_2$ is selected from:

a) hydrogen, provided that R$_2$ is not hydrogen if X is —S(=O)—, —SO$_2$—, —OC(=O)—, —OC(=O)NR$_d$—, or —S(=O)$_2$NR$_d$—;

b) alkyl or substituted alkyl, alkenyl or substituted alkenyl, and alkynyl or substituted alkynyl, cycloalkyl or substituted cycloalkyl, cycloalkenyl or substituted cycloalkenyl; and c) heterocycle or substituted heterocycle, aryl or substituted aryl; except that $R_2$ is absent if X is halogen, nitro, or cyano;

$R_1$ and $R_2$ together may optionally form a 3-7 membered optionally substituted carbocyclic ring or 3-7 membered optionally substituted heterocyclic ring;

D is CHO, CN, C(=O)$R_a$, C(=O)O$R_e$, or C(=O)N$R_bR_c$;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are each independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

comprising:

reacting a compound of formula I,

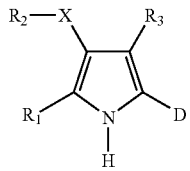

I with a benzoyl hydroxyl amine of formula III,

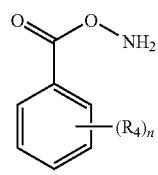

III wherein $R_4$ is nitro, cyano, halogen, OMe, or OEt, and n is 1, 2, or 3;

in the presence of a base to form the compound of formula II.

2. The method of claim 1, wherein the benzoyl hydroxyl amine of formula III is prepared by reacting a pharmaceutically acceptable salt of the benzoyl hydroxyl amine with a base.

3. The method of claim 1, wherein the benzoyl hydroxyl amine of formula III is prepared by reacting a salt of formula IV with a base,

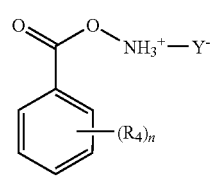

IV wherein:

$R_4$ is nitro, cyano, halogen, OMe, or OEt, n is 1, 2, or 3;

Y is MeSO$_3$—, EtSO$_3$—, 4-Me-PhSO$_3$—,

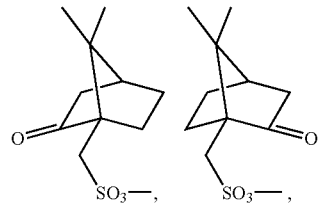

4-NO$_2$—PhSO$_3$—, CF$_3$SO$_3$—, —Cl, —H$_2$PO$_4$, —NO$_3$, —HSO$_4$, PhSO$_3$—, or —Br.

4. A method for preparing a compound of formula V,

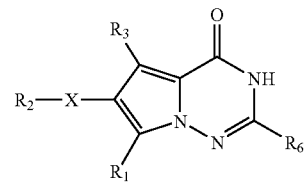

V wherein:

$R_1$ and $R_3$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, O$R_a$, S$R_a$, S(=O)$R_e$, S(=O)$_2R_e$, P(=O)$_2R_e$, S(=O)$_2$O$R_e$, P(=O)$_2$O$R_e$, N$R_bR_c$, N$R_b$S(=O)$_2R_e$, N$R_b$P(=O)$_2R_e$, S(=O)$_2$N$R_bR_c$, P(=O)$_2$N$R_bR_c$, C(=O)O$R_e$, C(=O)$R_a$, C(=O)N$R_bR_c$, OC(=O)$R_a$, OC(=O)N$R_bR_c$, N$R_b$C(=O)O$R_e$, N$R_d$C(=O)N$R_bR_c$, N$R_d$S(=O)$_2$N$R_bR_c$, N$R_d$P(=O)$_2$N$R_bR_c$, N$R_b$C(=O)$R_a$, or N$R_b$P(=O)$_2R_e$;

X is —O—, —OC(=O)—, —S—, —S(=O)—, —S(=O)$_2$—, —C(=O)—, —C(=O)O—, —N$R_d$—, —N$R_d$C(=O)—, —C(=O)N$R_d$—, —N$R_d$C(=O)N$R_d$—, —N$R_d$C(=O)O—, —OC(=O)N$R_d$—, —N$R_d$S(=O)$_2$—, —N$R_d$S(=O)$_2$N$R_d$—, —S(=O)$_2$N$R_d$—, halogen, nitro, cyano, or a bond;

$R_2$ is selected from:

a) hydrogen, provided that $R_2$ is not hydrogen if X is —S(=O)—, —SO$_2$—, —OC(=O)—, —OC(=O)N$R_d$—, or —S(=O)$_2$N$R_d$—;

b) alkyl or substituted alkyl, alkenyl or substituted alkenyl, and alkynyl or substituted alkynyl, cycloalkyl or substituted cycloalkyl, cycloalkenyl or substituted cycloalkenyl; and c) heterocycle or substituted heterocycle, aryl or substituted aryl;

except that $R_2$ is absent if X is halogen, nitro, or cyano;

$R_1$ and $R_2$ together may optionally form a 3-7 membered optionally substituted carbocyclic ring or 3-7 membered optionally substituted heterocyclic ring;

$R_6$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle or substituted heterocycle;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are each independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

comprising:

(a) reacting a compound of formula I,

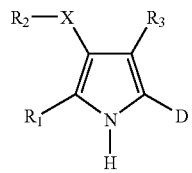

I wherein $R_1$, X, $R_2$ and $R_3$ are defined as hereinabove, and D is —C(=O)OR$_p$ wherein R$_p$ is selected from H, $C_1$-$C_6$ alkyl, or aryl;

with a benzoyl hydroxyl amine of formula III in the presence of a base,

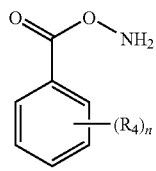

III wherein $R_4$ is H, nitro, cyano, halogen, $C_1$-$C_4$ alkyl, OMe, OEt, and n is 1, 2, or 3;

to form a compound of formula II,

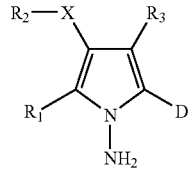

II wherein $R_1$, X, $R_2$, $R_3$ and D are defined as hereinabove; and (b) further reacting the compound of formula II with an amide of formula $R_6C(=O)NH_2$, wherein $R_6$ is defined as hereinabove, to form the compound of formula V.

5. The method of claim 4, wherein the benzoyl hydroxyl amine of formula III is prepared by reacting a pharmaceutically acceptable salt of the benzoyl hydroxyl amine with a base.

6. The method of claim 4, wherein the benzoyl hydroxyl amine of formula III is prepared by reacting a salt of formula IV with a base,

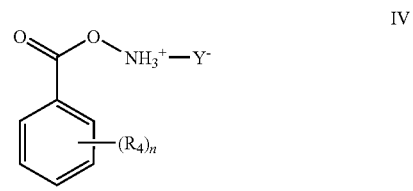

IV wherein:

$R_4$ is nitro, cyano, halogen, OMe, or OEt, n is 1, 2, or 3; and

Y is MeSO$_3$—, EtSO$_3$—, 4-Me-PhSO$_3$—,

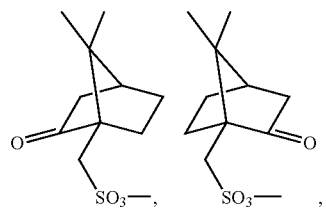

4-NO$_2$-PhSO$_3$—, CF$_3$SO$_3$—, —Cl, —H$_2$PO$_4$, —NO$_3$, —HSO$_4$, PhSO$_3$—, or —Br.

7. The method of claim 4, wherein $R_6$ is H, and R$_p$ is Me or Et.

8. The method of claim 4, wherein the benzoyl hydroxyl amine of formula III is:

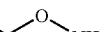

9. The method of claim 4, wherein X is —C(=O)O—, $R_2$ is Et, $R_3$ is Me, $R_1$ is H, D is —C(=O)OEt and $R_6$ is H.

* * * * *

UNITED STATES PATENT AND TRADEMARK OFFICE
CERTIFICATE OF CORRECTION

PATENT NO. : 7,534,881 B2  
APPLICATION NO. : 11/168682  
DATED : May 19, 2009  
INVENTOR(S) : Zhongping Shi et al.

Page 1 of 1

It is certified that error appears in the above-identified patent and that said Letters Patent is hereby corrected as shown below:

In the Claims:

Claim 1:
  Column 14, lines 60 and 61, change "—$NR_dC(=O)NR_d$ , $NR_dC(=O)O$ , $OC(=O)NR_d$ ," to -- —$NR_dC(=O)NR_d$—, —$NR_dC(=O)O$—, —$OC(=O)NR_d$—, --.
  Column 14, line 62, change "—$N_dS(=O)_2NR_d$—," to -- —$NR_dS(=O)_2NR_d$—, --.

Claim 4:
  Column 16, line 46, change "—$OC(=O)N_d$—," to -- —$OC(=O)NR_d$—, --.
  Column 17, line 44, before "nitro," delete "H,".
  Column 17, line 44, before "OMe," delete "$C_1$–$C_4$ alkyl,".

Claim 9:
  Column 18, line 55, change "—$C(=O)O$—,$R_2$" to -- —$C(=O)O$—, $R_2$ --.

Signed and Sealed this  
Eighth Day of May, 2012

David J. Kappos  
*Director of the United States Patent and Trademark Office*